(12) United States Patent
Kana

(10) Patent No.: US 7,604,640 B2
(45) Date of Patent: Oct. 20, 2009

(54) DEVICE AND SYSTEM FOR APPLYING ROTARY IMPACT

(75) Inventor: Richard J. Kana, Lexington, TX (US)

(73) Assignee: Zimmer Spine Austin, Inc., Austin, TX (US)

( * ) Notice: Subject to any disclaimer, the term of this patent is extended or adjusted under 35 U.S.C. 154(b) by 113 days.

(21) Appl. No.: 11/763,296

(22) Filed: Jun. 14, 2007

(65) Prior Publication Data
US 2008/0308600 A1 Dec. 18, 2008

(51) Int. Cl.
*A61B 17/58* (2006.01)
*B25D 15/02* (2006.01)
*B25D 21/02* (2006.01)

(52) U.S. Cl. .................. 606/99; 173/93; 173/93.5; 173/94; 173/97; 173/1; 81/463; 81/465; 81/466

(58) Field of Classification Search .............. 173/1, 173/13, 21, 90, 93, 93.5, 94; 227/2, 19; 81/463, 465, 466; 606/99
See application file for complete search history.

(56) References Cited

U.S. PATENT DOCUMENTS

| | | | | |
|---|---|---|---|---|
| 2,461,491 | A | * | 2/1949 | Booth ................... 73/862.21 |
| 4,036,057 | A | * | 7/1977 | Morais ................... 73/587 |
| 4,606,343 | A | * | 8/1986 | Conta et al. ............ 227/178.1 |
| 4,653,359 | A | * | 3/1987 | Liao ...................... 81/475 |
| 5,005,749 | A | * | 4/1991 | Aranyi ................... 227/19 |
| 5,012,709 | A | * | 5/1991 | Su ........................ 81/466 |
| 5,333,773 | A | * | 8/1994 | Main et al. .............. 227/179.1 |
| 5,507,830 | A | | 4/1996 | DeMane et al. |
| 5,535,648 | A | * | 7/1996 | Braun et al. ............ 81/63.1 |
| 5,620,445 | A | | 4/1997 | Brosnahan et al. |
| 5,915,616 | A | * | 6/1999 | Viola et al. ............. 227/179.1 |
| 5,941,885 | A | | 8/1999 | Jackson |
| 6,406,480 | B1 | | 6/2002 | Beyar et al. |
| 6,554,830 | B1 | | 4/2003 | Chappius |
| 6,565,572 | B2 | | 5/2003 | Chappius |
| 6,663,642 | B2 | | 12/2003 | Beyar et al. |
| 6,814,159 | B1 | * | 11/2004 | Huang .................... 173/205 |
| 7,014,023 | B1 | * | 3/2006 | Gauthier ................. 192/43.1 |
| 7,107,883 | B2 | * | 9/2006 | Casutt ..................... 81/467 |
| 7,168,604 | B2 | * | 1/2007 | Milliman et al. ......... 227/176.1 |
| 7,303,106 | B2 | * | 12/2007 | Milliman et al. ......... 227/175.1 |
| 7,413,065 | B2 | * | 8/2008 | Gauthier ................. 192/43.1 |
| 7,430,945 | B2 | * | 10/2008 | Gauthier et al. ......... 81/467 |
| 2001/0021852 | A1 | | 9/2001 | Chappius |
| 2002/0013608 | A1 | | 1/2002 | ElAttrache et al. |
| 2004/0210227 | A1 | | 10/2004 | Trail et al. |
| 2005/0023325 | A1 | * | 2/2005 | Gresham et al. ......... 227/176.1 |
| 2005/0149031 | A1 | | 7/2005 | Ciccone et al. |
| 2006/0069391 | A1 | | 3/2006 | Jackson |
| 2006/0074421 | A1 | | 4/2006 | Bickley et al. |
| 2006/0081553 | A1 | | 4/2006 | Patterson et al. |

(Continued)

*Primary Examiner*—Rinaldi I. Rada
*Assistant Examiner*—Gloria R. Weeks
(74) *Attorney, Agent, or Firm*—Sprinkle IP Law Group

(57) ABSTRACT

A device and system for applying rotational impact to screws implanted in bony tissues. Specifically, embodiments of the present disclosure may provide medical professionals the ability to apply impact forces and torques to a threaded member in a rotational plane such that the surrounding tissues are not damaged from an axial impact or excessive rotational forces. The rotary impact driver may be used with thin and flexible shafts for percutaneous procedures.

14 Claims, 4 Drawing Sheets

U.S. PATENT DOCUMENTS

| | | |
|---|---|---|
| 2006/0200150 A1 | 9/2006 | Homaki et al. |
| 2007/0032162 A1 | 2/2007 | Jackson |
| 2008/0078806 A1* | 4/2008 | Omaits et al. ............ 227/181.1 |
| 2008/0234083 A1* | 9/2008 | Haenbeukers et al. ....... 474/135 |
| 2009/0025518 A1* | 1/2009 | Gauthier et al. ............... 81/467 |

* cited by examiner

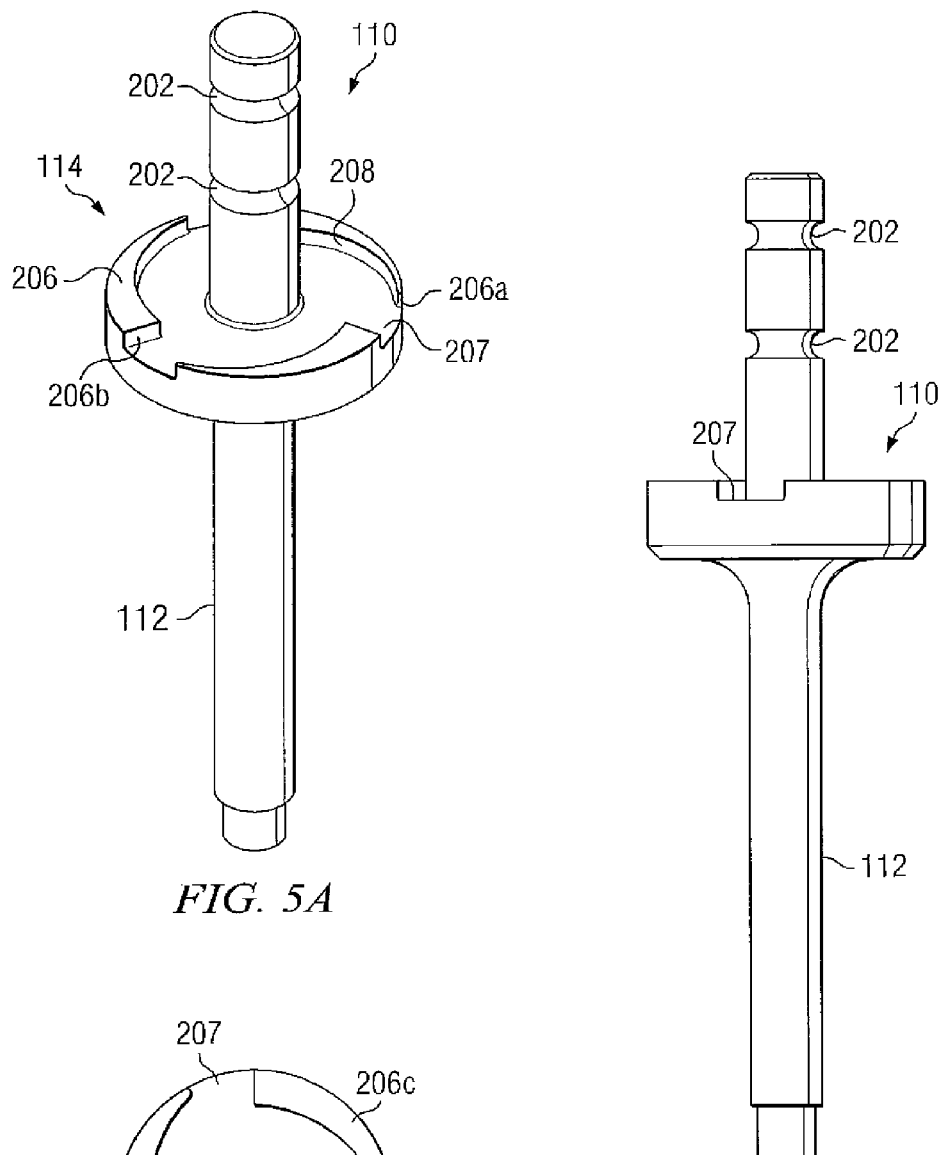
FIG. 5A
FIG. 5B
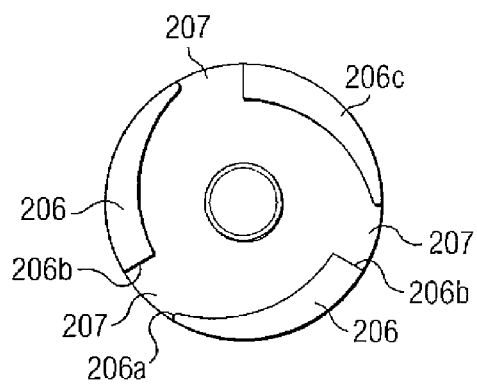
FIG. 5C

DEVICE AND SYSTEM FOR APPLYING ROTARY IMPACT

TECHNICAL FIELD OF THE DISCLOSURE

This disclosure relates generally to tools for implanting and removing screws in bony tissues within a body, and in particular to a device and system for applying rotational impact to a screw

BACKGROUND

In medical situations, it is sometimes necessary to remove screws, anchors, or other threaded members from bony tissues. The removal process may be difficult because of the general effects from implanting anchors (e.g. corrosion, fusion) and the particular effects of the patient's health (e.g. bone density, brittleness.)

Extreme rotational force is required to break these screws free from the bone during revision surgery, to such a degree that it is common for the tips of the driver to bend, twist, or otherwise deform, ultimately causing instrument failure.

SUMMARY OF THE DISCLOSURE

Impact tools generally deliver a high-torque output (impact) useful for loosening frozen fasteners such as bolts, screws, and other threaded members. One common form of impact tool is designed such that when a hammer or mallet strikes the proximal end, the distal tip is forced into the screw and the screw is simultaneously forced to rotate some degree. This type of impact tool is not generally used in surgical procedures, because there is a large axial impact on the patient to produce a relatively small rotation of the screw. The axial impact of the blow might result in more damage to the patient and may also break or otherwise damage the screw. A second type of impact tool commonly seen is the electric or air-powered impact tool commonly used in automotive settings, such as to remove frozen lug nuts from wheels. However, these tools are designed to provide large torques which can harm the patient, are generally used on nuts and bolts because there is a minimum torque needed, and the tools are bulky, which is undesirable in minimally invasive surgery (MIS) procedures.

Embodiments of the present disclosure provide devices, systems and methods for removing screws, anchors, and other threaded members from bony tissues by applying a rotational impact to a threaded member. Embodiments of the present disclosure also may be operated by hand power alone, so there is more controlled application of impact forces. Embodiments of the present disclosure also allow for much smaller impact torque because there is no minimum torque needed for operation.

In one embodiment of the present disclosure, an impact driver for applying a rotational impact to a screw or anchor includes a torsion spring retained in a spring cavity positioned on the longitudinal axis of the impact driver. The torsion spring has a first end fixedly connected to the impact driver body and a second end that may move relative to the impact driver body. The body has a shaft cavity disposed on the longitudinal axis for retaining at least a portion of a shaft, and the shaft assembly comprises a shaft having a proximal end adapted for rotatable connection to the body, a distal end adapted for connection to a driver tip, and an impact disk connected to the shaft comprising one or more contact sections defined by an arc length and profile for slidable contact with the second end of the torsion spring and one or more non-contact sections of selected arc length separating the contact sections. Rotation of the body about the shaft when the second end is in slidable contact with a contact section changes the torsion spring configuration to generate potential energy in the torsion spring, and further rotation of the body about the shaft when the second end transitions across a non-contact section converts the potential energy in the torsion spring to a rotational impact on the next contact section, resulting in an impact that is translated by the shaft to an anchor. The rotary impact device may further include a handle connected to the body for hand-powered operation, or the body may be further configured for detachable connection to an apparatus for rotating the body at a selected rate, such as a powered drill. The contact sections may have variable contact profiles, and may be designed configured for two-way operation. In some embodiments the contact sections may have a gear-tooth profile, a saw-tooth profile, or a hyperbolic profile. In some embodiments the shaft is flexible. In some embodiments the second end of the torsion spring comprises a weight to provide additional impact force.

Another embodiment of the present disclosure includes a method for applying rotational impact to threaded members by detachably connecting a driver tip for a rotary impact driver to the head of the anchor and rotating the driver such that impact forces are generated which translate into impact torques on the anchor. To accomplish this goal, the rotary impact driver has a spring cavity disposed on a longitudinal axis for retaining at least a portion of the torsion spring with an adaptation for fixed connection to the first end of the torsion spring, and a shaft cavity disposed on the longitudinal axis for retaining at least a portion of a shaft assembly. A shaft assembly has a shaft with a proximal end configured for rotatable connection to the body, a distal end configured for connection to a driver tip, and an impact disk connected to the shaft. The impact disk has one or more contact sections defined by an arc length and profile for slidable contact with the second end of the torsion spring and one or more non-contact sections of selected arc length separating the one or more contact sections. By rotating the body about the shaft when the second end is in contact with a contact section, the torsion spring configuration changes to generate potential energy in the torsion spring. Further rotating the body about the shaft such that the second end transitions across a non-contact section converts the potential energy in the torsion spring into a rotational impact on the shaft. In some embodiments, the rotary impact driver comprised a handle attached to the body such that the body is rotated by rotating the handle. In some embodiments, the rotary impact driver has a proximal end configured for attaching a power tool to the body such that the body is rotated by operation of the power tool, such as an electric drill.

The present disclosure overcomes prior art methods and systems for removing screws from bony tissue by applying the impact in a rotational direction, thus reducing the effects on the bony tissue.

The present disclosure overcomes prior art devices and systems for removing screws from bony tissue by enabling one-handed operation to remove screws and further enabling percutaneous operation. Embodiments of the present disclosure may be used to apply torques in clockwise or counter-clockwise direction, allowing surgeons to apply torques for implanting or removing threaded anchors, screws, and the like from bony tissue.

These, and other, aspects of the disclosure will be better appreciated and understood when considered in conjunction with the following description and the accompanying drawings. The following description, while indicating various embodiments of the disclosure and numerous specific details thereof, is given by way of illustration and not of limitation. Many substitutions, modifications, additions or rearrangements may be made within the scope of the disclosure, and the disclosure includes all such substitutions, modifications, additions or rearrangements.

BRIEF DESCRIPTION OF THE FIGURES

FIG. 5A is a reference view of one embodiment of a shaft assembly for use in a rotary impact driver;

FIG. 5B is a side view of one embodiment of a shaft assembly for use in a rotary impact driver; and FIG. 5C is a top view of one embodiment of a shaft assembly for use in a rotary impact driver.

DETAILED DESCRIPTION OF THE DISCLOSURE

Figure 1A:
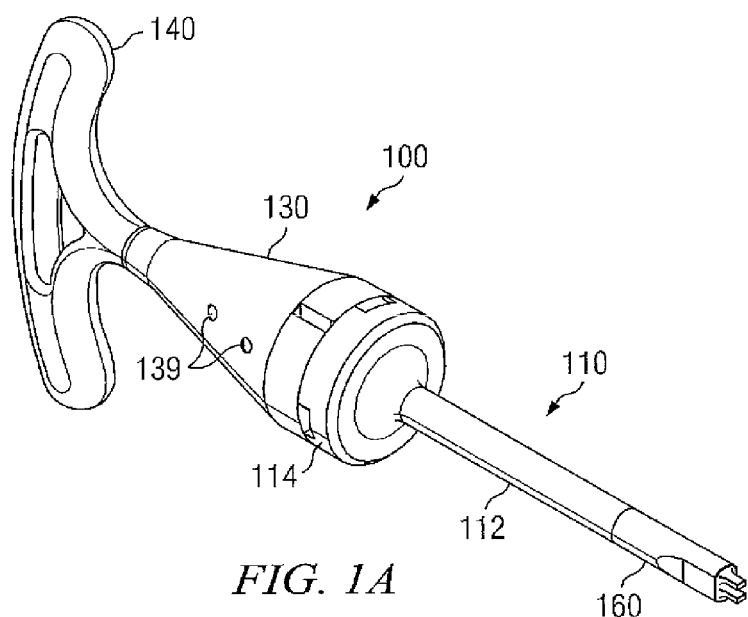
FIG. 1A is a reference view of one embodiment of a rotary impact driver.

The disclosure and the various features and advantageous details thereof are explained more fully with reference to the non-limiting embodiments that are illustrated in the accompanying drawings and detailed in the following description. Descriptions of well known starting materials, processing techniques, components and equipment are omitted so as not to unnecessarily obscure the disclosure in detail. Skilled artisans should understand, however, that the detailed description and the specific examples, while disclosing preferred embodiments of the disclosure, are given by way of illustration only and not by way of limitation. Various substitutions, modifications, additions or rearrangements within the scope of the underlying inventive concept(s) will become apparent to those skilled in the art after reading this disclosure.

Reference is now made in detail to the exemplary embodiments of the disclosure, examples of which are illustrated in the accompanying drawings. Wherever possible, the same reference numbers will be used throughout the drawings to refer to the same or like parts (elements.)

The devices and methods of the disclosure may be particularly useful for removing screws from bony tissue, particularly in MIS procedures and thus it is in this context that embodiments of the disclosure may be described it will be appreciated, however, that embodiments of the systems and methods of the present disclosure may be applicable for applying rotational impact useful for engaging or removing anchors, bolts or other threaded members generally defined as having a shank with a helically wound feature (thread) with a profile, pitch, thread count, and other characteristics for inserting and advancing the shank into a selected material. The thread may or may not be continuous, and may have a square profile, a V-shaped profile, or some other standard or proprietary profile. The pitch may be a standard or proprietary pitch advantageous for a particular material, which may include bone, muscle, or other tissue, and may further include plastics, polymers, and other materials. In preferred embodiments, anchors may be used for inserting and advancing into bony tissue such as the cancellous tissues found in the vertebral bodies of the spine. Bone screws, both solid and cannulated, are examples of devices having a shank with a thread and which are useful for inserting and advancing into bony tissue.

One of the reasons that embodiments of the present disclosure may be useful in the removal of screws from bony tissue is the minimal effect on the tissue. Any time a bone is subjected to a direct impact force (such as an axial impact on a screw), the possibility for fracture, cracking, chipping, and splintering exists, as well as secondary effects such as bruising, pain, soreness, and discomfort and the adverse effects that may occur to the spinal cord, discs, facet joints, blood vessels, and the like. Thus, it is desirable to reduce or eliminate the need to axially impact screws that have seized in bony tissue.

To achieve these goals, embodiments of the present disclosure utilize the rotation of the tool handle to produce an impact in a purely rotational plane such that a radial impact force is focused on the screw and no axial impact is exerted on the bony tissue.

More particularly, embodiments of such a rotary impact driver allow medical professionals to use one-handed operations to apply a rotational impact to an anchor. Furthermore, the design is advantageous for percutaneous operations, by minimizing the size and number of incisions needed for selected medical procedures, by reducing the tool size for easier manipulation, and by reducing the likelihood that the surrounding tissues may be damaged.

Embodiments of the present disclosure may be better explained with reference to the accompanying figures which depict devices and systems for generating rotary impact forces.

FIG. 1A is a reference view of one embodiment of a rotary impact driver 100. In this embodiment, rotary impact driver 100 has a handle 140 configured for rigid attachment to a body 130 for applying a rotational torque. A shaft assembly 110 having a shaft 112 and an impact disk 114 may be rotatably connected to body 130 and in select contact with a torsion spring inside body 130, such that rotation of the body 130 about the shaft assembly 110 generates an impact torque. Driver tip 160 is selectively and detachably connected to end of shaft assembly 110 to enable a surgeon to apply the impact torque to an anchor in bony tissue. Advantageously, the diameter of the shaft 112 may be smaller than impact tools that may be exposed to an axial impact force. This may have a secondary effect of requiring less clearance for the surgeon to maintain visual contact with a screw being inserted into or removed from bony tissues. Shaft assembly 110, body 130, handle 140, and driver tip 160 may further be cannulated to allow other tools, lighting, or the like to be passed through rotary impact driver 100. Body 130 further comprises one or more openings 139 for receiving one or more assembly pins or the like (discussed below).

Figure 1B:
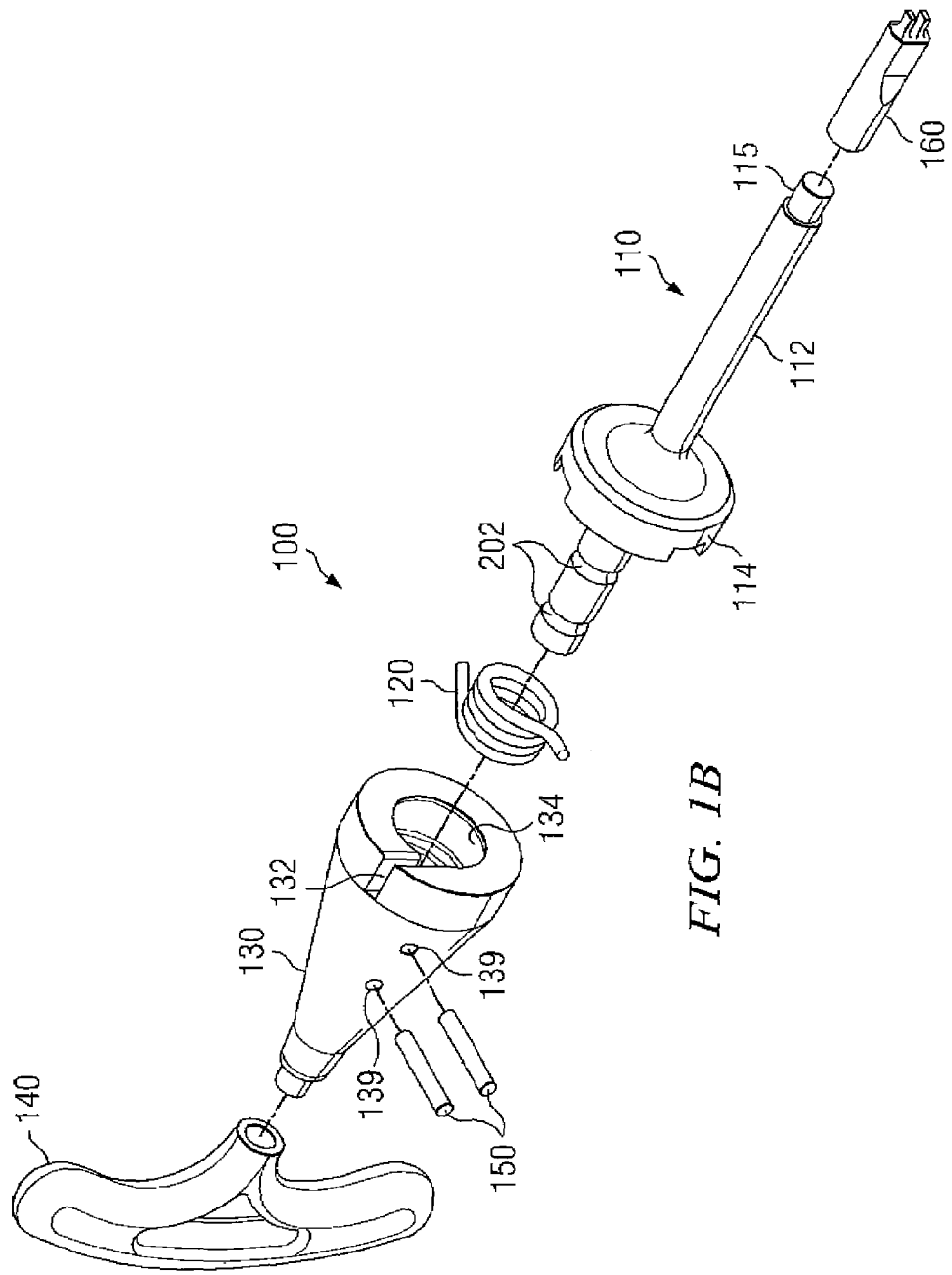
FIG. 1B is an exploded view of one embodiment of a rotary impact driver.

FIG. 1B is an exploded view of a rotary impact driver 100 such as depicted in FIG. 1A. In this figure, rotary impact driver 100 includes handle 140 having a distal end 141 that is attached or otherwise rigidly connected to proximal end 131 of body 130. A torsion spring 120 located inside spring cavity 134 in body 130 has a first end 123 connected to body 130 which is configured, such as with opening 132 configured to receive and securely maintain a portion of a torsion spring 120, for fixedly connecting torsion spring 120 to body 130. For purposes of this document, the term torsion spring generally refers to a device or system capable of resisting rotational forces (torques) or storing the energy caused by the rotation into a form of potential energy. A torsion spring may be comprised of a single coil, may be configured with two or more coils capable of functioning with the same effect as a single coil, or may be configured with two or more coils to provide torsion when rotated in either direction. Torsion spring 120 is positioned in spring cavity 134 with one end of torsion spring 120 connected to opening 132 such that shaft assembly 110 may be at least partially inserted into body 130 to align one or more grooves 202 on shaft assembly 110 with one or more openings 139 on body 130 for one or more assembly pins 150. A second end of torsion spring 120 preferably is configured for slidable contact with contact disk 114 such that rotation of torsion spring 120 periodically imparts a rotational impact on contact disk 114 which transmits the impact torque through shaft 112 to a driver tip 160 (discussed below).

Still referring to FIGS. 1A and 1B, shaft 110 also has a distal end 115 adapted for selective and detachable connection with driver tip 160 configured with features 161 for attachment to a bone crew, anchor, or other device requiring some torque but without an associated axial force. In some embodiments, driver tip 160 and distal end 115 of shaft 110 may be manufactured separately and then joined to form a single rigid unit, or maybe manufactured together, such as by casting or machining. In some embodiments, shaft 110 and driver tip 160 may be manufactured as a single unit. Driver tip 160 may have standard features such as an internal hex, key-style profile (not shown), or may have proprietary features, designs or configurations 161.

Figure 2A:
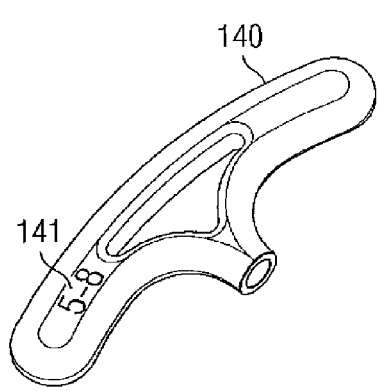
FIG. 2A is a reference view of a handle for use in one embodiment of a rotary impact driver.
Figure 2B:
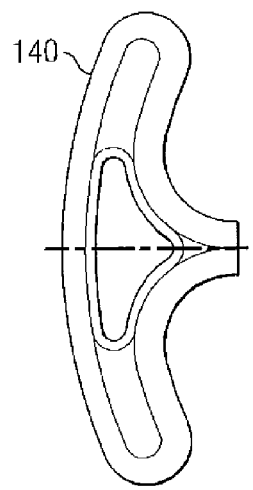
FIG. 2B is a side view of a handle for use in one embodiment of a rotary impact driver.

Referring to FIGS. 2A and 2B, handle 140 has distal end 141 for rigid attachment to the proximal end of a tool, such as proximal end 131 of body 130 in FIG. 1B, and allows a surgeon to manually apply a torque so that embodiments of the present disclosure may remove a threaded member from bony tissue by rotating the threaded member to disengage threads from the bony tissue, and may further be used to insert and advance a threaded member into bony tissue by rotating the threaded member to engage the bony tissue. Handle 140 may be configured in any shape that allows a surgeon to apply a torque to body 130. In some embodiments, handle 140 may be T-shaped, L-shaped, ball-type, in-line driver-type similar to common screwdrivers, and may be configured for ergonomic considerations such as the curved T-shaped handle shown, or for a desired mechanical advantage. Handle 140 may be manufactured from any material including but not limited to stainless steel, titanium, aluminum such as 6061-T6 aluminum, metal alloys, and polymers that can withstand the torque applied by a surgeon. Material for handle 140 is further selected for compatibility with body 130 to prevent corrosion from dissimilar metals or other undesirable effects. Handle 140 may further include a ratchet mechanism for advantageously allowing surgeons to utilize one-handed operations without the need to constantly reposition their hands. In some embodiments, distal end 141 of handle 140 is mechanically, chemically, or thermally permanently attached to body 130. For example, handle 140 may be press fit or threaded onto body 130, handle 140 may be glued or epoxied to body 130, or handle 140 may be welded or sweat-locked to body 130. Handle 140 may also be color-coded or otherwise marked, such as marking 141, to indicate information about rotary impact driver 100. For example, a kit may contain more than one rotary impact driver 100, with each rotary impact driver 100 having information stamped into the material to provide some indication as to how much rotational impact will be imparted on a threaded member by that rotary impact driver 100. In FIG. 2A, marking 141 may indicate that the rotary impact driver 100 is pre-set to deliver a rotary impact torque value of 5-8 inch-pounds, a part in a kit, a manufacturing batch number, or other information.

Figure 3A:
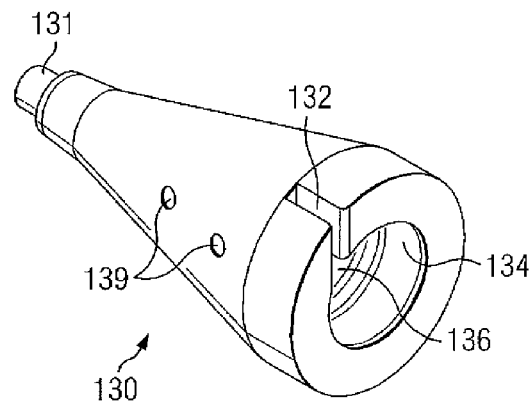
FIG. 3A is a reference view of a body for use in one embodiment of a rotary impact driver.
Figure 3B:
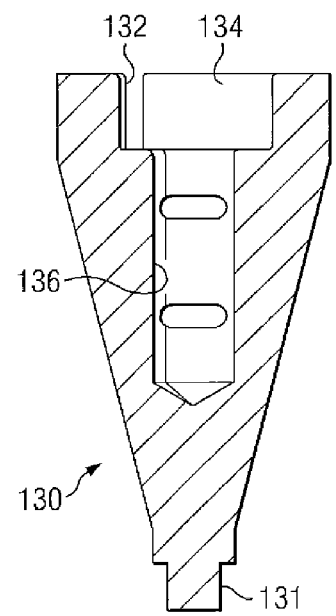
FIG. 3B is a cross-section view of a body for use in one embodiment of a rotary impact driver.
Figure 3C:
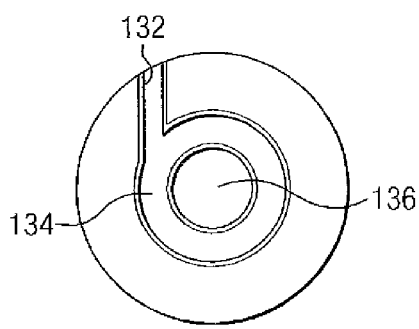
FIG. 3C is a bottom view of a body for use in one embodiment of a rotary impact driver.

Referring now to FIGS. 3A, 3B and 3C, body 130 (in cooperation with shaft assembly 110, discussed below) supports and maintains a torsion spring (such as torsion spring 120 in FIG. 1B) in a desired configuration relative to shaft assembly 110, and includes a spring cavity 134 for retaining at least a portion of torsion spring 120, and a shaft cavity 136 for retaining a portion of shaft 100 about the longitudinal axis of body 130. Body 130 is also configured with a feature such as opening 132 for retaining one end of torsion spring 120. Body 130 may be manufactured from any material (including but not limited to stainless steel, titanium, aluminum such as 6061-T6, metal alloys, and polymers) that can withstand torque applied by a surgeon. Material for body 130 may be selected for compatibility with handle 140, shaft assembly 110, and torsion spring 120 to prevent corrosion from dissimilar metals or other undesirable effects. In some embodiments, proximal end 131 of body 130 is configured for rigid connection to distal end 141 of handle 140. In some embodiments, body 130 is adapted for connection to an electric drill or other equipment operable to provide rotational velocity.

Body 130 and shaft assembly 110 are generally able to rotate freely about each other, but preferably not disconnect during surgery. To accomplish this, shaft assembly 110 and body 130 may be configured to allow a rotatable yet secure connection. For example, referring to FIGS. 1A-B and 3A, in some embodiments the tips of assembly pins 150 inserted through openings 139 in body 130 may be configured to track or otherwise align in grooves 202 on shaft 112 to provide a secure connection that enables body 130 to rotate about shaft assembly 110 without disconnecting. In other embodiments (not shown), body 130 may have one or more grooves and shaft 112 may have one or more corresponding extensions or protrusions to enable body 130 to rotate securely about shaft assembly 110. Retaining rings, snap rings, and the like may also be used to effectively connect body 130 to shaft assembly 110 while maintaining rotational movement. Advantageously, embodiments of the present disclosure may be easily disassembled for cleaning and inspection, and torsion spring 120 may be removed or replaced (such as with torsion springs 120 having different spring constants for different applications) by removing assembly pins 150 from openings 139.

In FIG. 3B, body 130 is shown with spring cavity 134 and shaft cavity 136 extending partially along the longitudinal axis of body 130. However, body 130 may be cannulated to allow instruments, tools, lighting or the like to pass through body 130 for improved percutaneous procedures.

Figure 4A:
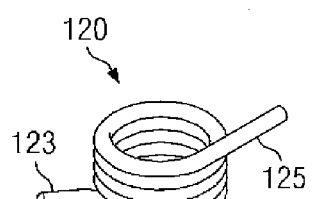
FIG. 4A is a reference view of a torsion spring for use in one embodiment of a rotary impact driver.
Figure 4B:
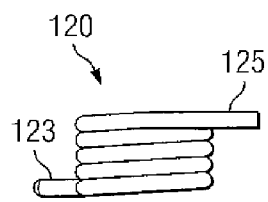
FIG. 4B is a side view of a torsion spring for use in one embodiment of a rotary impact driver.
Figure 4C:
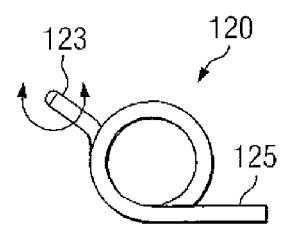
FIG. 4C is a top view of a torsion spring for use in one embodiment of a rotary impact driver.

In FIG. 3C, spring cavity 134 and shaft cavity 136 are shown axially aligned with the longitudinal axis of body 130, and opening 132 is positioned based on the location and orientation of the first end of a torsion spring (such as shown in FIGS. 4A-C.

Referring to FIGS. 1A and 1B and 4A, 4B and 4C, torsion spring 120 sits in spring cavity 134 of body 130 with a first end 123 fixed to body 130 such as in opening 132 and a second end 125 free to turn about the longitudinal axis of body 130. Torsion springs 120 generally comprise a wire manufactured from metal such as music wire, chrome vanadium, stainless steel 302 or 17-7 (313) and are generally wound for clockwise or counterclockwise operation about the central axis. The wire has an associated wire diameter and is wound into a coil having an inside diameter and a body width, and leg lengths for first end 123 and second end 125. The inside diameter of torsion spring 120 is selectively larger than the outer diameter of shaft 112 such that shaft 112 provides support and stability to torsion spring 120. The body width of torsion spring 120 depends on the number of windings and the wire diameter. First end 123 and second end 125 of torsion spring 120 may be configured at a given angle to each other based on desired characteristics, and any angle is possible using the present disclosure.

The distance from the center of the coil to the end of first end 123 or second end 125 is the leg length, which provides the moment arm for any torque. Those skilled in the art will appreciate that the amount of potential energy stored in torsion spring 120 depends on the spring constant (which is determined based on at least the wire diameter, inside diameter of the coil, the body width, leg length, material, and temperature) and the deflection. As body 130 is turned by the surgeon (using handle 140 or some other tool connected to proximal end 131 of body 130), body 130 and the first end 123 of torsion spring 120 rotate about shaft 112, and the second end 125 of torsion spring 120 periodically deflects a selected angle, and releases from the deflected state to a free state to generate an impact on a portion or feature of shaft assembly 110 in the direction of rotation, thereby overcoming the effects of friction, corrosion, or other resistive forces on a threaded member. Second end 125 of torsion spring 120 may further have a thicker diameter or otherwise have weight added to produce a larger impact force. In some embodiments, torsion spring 120 may be manufactured with two or more coils. In some of these embodiments, the two or more coils may provide the functionality (such as a desired spring constant) of a single coil. In other embodiments, the two or more coils may be reversed to be able to generate rotational impacts in either direction of rotation.

Referring to FIGS. 1A-B and 5A-C, shaft assembly 110 includes an impact disk 114 having one or more contact sections 206 of selected arc length and profile for generating potential energy in torsion spring 120, and a corresponding number of non-contact sections 207 of selected arc length for translating the potential energy in torsion spring 120 into a form of kinetic energy useful for generating an impact. As body 130 rotates about shaft 112 such that the free end of the torsion spring (such as second end 125 of torsion spring 120 in FIGS. 4A-C) is in contact with a surface 208 of contact section 206, surface 208 of contact section 206 or geometry of contact section 206 or both retard the progression of second end 125 such that the effect of further turning body 130 results in the distortion of torsion spring 120 (e.g. a decrease in diameter and increase in body width), effectively storing potential energy in torsion spring 120.

Shaft 112 and impact disk 114 may be manufactured separately and then joined to form a single rigid unit, or may be manufactured together as a single shaft assembly 110, such as by casting or machining. Shaft 112 and impact disk 114 may be manufactured from any material (including but not limited to stainless steel, titanium, aluminum, metal alloys, and polymers) that can withstand torque applied by a surgeon, torque or potential energy resulting from one or more torsion springs 120 in slidable contact with one or more contact sections 206, and impact resulting from one or more torsion springs 120 releasing the potential energy when transitioning across non-contact sections 207. Materials for shaft 112 and impact disk 114 may be further selected for compatibility with body 130, torsion spring 120, and driver tip 160 to prevent corrosion from dissimilar metals or other undesirable effects, and for biocompatibility to enable the surgeon to access screws in MIS procedures.

Shaft 112 may also be a flexible shaft or have a joint such as a universal joint (not shown) such that embodiments of the present disclosure may be oriented at some angle to the longitudinal axis of an anchor yet still provide rotary impact to the anchor without imparting an axial force on the anchor. In other words, using embodiments of the present disclosure, surgeons may apply a rotational impact to remove anchors, screws, or other threaded members from bony tissue without the need to be positioned directly over the anchor. Prior art impact tools that require a hammer or mallet to strike the impact tool are unable to utilize flexible, angled, or jointed shafts because the axial force required to generate the rotational impact would be directed off-axis and could potentially do more damage to the screw or the patient. Using prior art methods then generally require the surgeon to position a screw removal tool on almost the same axis as the screw, or risk the possibility that the driver tip will disconnect from the anchor or damage the anchor head, or both. Embodiments of the present disclosure advantageously may be effective at off-axis angles for removing screws or other threaded members because axial forces are not necessary.

Contact sections 206 generally comprise a leading edge 206a and a trailing edge 206b and may have any profile that allows for slidable contact between surface 208 and second end 125 of torsion spring 120 such that torsion spring 120 inside body 130 may still rotate about shaft 112, but the rotation is resisted either by friction or geometry such that potential energy is stored in torsion spring 120. In some embodiments, contact sections 206 have a constant radius, such as a stepped radius, such that leading edge 206a and trailing edge 206b have the same thickness. In other embodiments, contact sections 206 have variable radii, such as a hyperbolic, sinusoidal, or other continuous profile or a sawtooth, stepped, geared or other discrete profile.

In some embodiments, non-contact sections 207 may be provided by machining material from contact disk 114 (such as non-contact sections 207 shown in FIG. 5A). In other embodiments, contact disk 114 may have a continuous exterior surface and non-contact sections 207 may be manufactured with a radius greater than the length of second end 125 of toroidal spring 120, which allows potential energy stored in torsion spring 120 to be converted back to a torque through the sudden impact of the second end 125 of torsion spring 120 on the next contact section 206.

In FIGS. 5A and 5C, three contact sections 206 are depicted having variable radii defined by ninety degree arc lengths and with a variable radius definable in terms of hyperbolic functions, and three non-contact sections 207 defied by thirty degree arc lengths, totaling 360 degrees. By changing the number, arc length, and profile of contact sections 206 and the number and arc length of non-contact sections 207, a desired impact sequence is produced. In some embodiments, the profile of contact section 206 may be symmetric (not-shown) for two-way operation, such that an impact may be generated during implantation.

The number and arc length of contact sections 206 and non-contact sections 207 will determine the angle of rotation required to generate an impact. For example, in the embodiments shown, for every revolution of body 130 about shaft 110, an impact force is generated three times. By increasing the number of contact sections 206 and non-contact sections 207 on impact disk 114, the angle of rotation needed to generate an impact is decreased, making it easier for a surgeon to use one-handed operation in applying a rotary impact to a screw.

In the foregoing specification, the disclosure has been described with reference to specific embodiments. However, one of ordinary skill in the art appreciates that various modifications and changes can be made without departing from the scope of the disclosure as set forth in the claims below. Accordingly, the specification and figures are to be regarded in an illustrative rather than a restrictive sense, and all such modifications are intended to be included within the scope of disclosure.

Benefits, other advantages, and solutions to problems have been described above with regard to specific embodiments. However, the benefits, advantages, solutions to problems, and any component(s) that may cause any benefit, advantage, or solution to occur or become more pronounced are not to be construed as a critical, required, or essential feature or component of any or all the claims.

What is claimed is:

1. A device for applying rotary impact comprising:
   a torsion spring defined by a diameter and width and having a first end and a second end;
   a body comprising
      a proximal end configured for rigid attachment to a tool;
      a spring cavity disposed on a longitudinal axis for retaining at least a portion of the torsion spring;
      an opening configured for fixed connection to the first end of the torsion spring; and
      a shaft cavity disposed on the longitudinal axis for retaining at least a portion of a shaft;
   a shaft assembly comprising:
      a shaft comprising a proximal end adapted for rotatable connection to the body and a distal end adapted for connection to a driver tip; and
      an impact disk rigidly connected to the shaft comprising one or more contact sections defined by an arc length and profile for slidable contact with the second end of the torsion spring and one or more non-contact sections of selected arc length separating the one or more contact sections,
   wherein rotation of the body about the shaft when the second end is in contact with a first contact section changes the torsion spring configuration to generate potential energy in the torsion spring, and
   wherein further rotation of the body about the shaft causes the second end to be in a non-contact section, wherein the torsion spring is configured to convert the generated potential energy into kinetic energy when the second end is in the non-contact section, causing the second end to transition across the non-contact section and contact a second contact section, wherein the contact with the second contact section converts the kinetic energy in the torsion spring to a rotary impact on the shaft.

2. The device of claim 1, further comprising a handle having a distal end configured for rigid connection to the proximal end of the body.

3. The device of claim 1, wherein the contact sections have variable contact profiles.

4. The device of claim 3, wherein the contact sections comprise a profile configured for two-way operation.

5. The device of claim 1, wherein the shaft assembly comprises a flexible shaft operable to transmit rotational impacts at an angle to the longitudinal axis of the body.

6. The device of claim 1, wherein the second end of the torsion spring comprises a weight.

7. device of claim 1, wherein the torsion spring comprises two or more torsion springs.

8. A method for applying rotational impact to a bone anchor comprising:
   detachably connecting a driver tip for a rotary impact driver to the head of a bone anchor, wherein the rotary impact driver comprises
      a torsion spring having a first end and a second end;
      a body comprising
         a spring cavity disposed on a longitudinal axis for retaining at least a portion of the torsion spring;
         an adaptation for fixed connection to the first end of the torsion spring; and
         a shaft cavity disposed on the longitudinal axis for retaining at least a portion of a shaft;
      a shaft assembly comprising
         a shaft comprising a proximal end adapted for rotatable connection to the body and a distal end adapted for connection to the driver tip; and
         an impact disk rigidly connected to the shaft comprising
            one or more contact sections defined by an arc length for slidable contact with the second end of the torsion spring and
            one or more non-contact sections of selected arc length separating the one or more contact sections;
   rotating the body about the shaft when the second end is in contact with a contact section, wherein such the torsion spring configuration changes to generate potential energy in the torsion spring; and
   further rotating the body about the shaft to cause the second end to be in a non-contact section, wherein the torsion spring is configured to convert the generated potential energy into kinetic energy when the second end is in the non-contact section, causing the second end to transition across the non-contact section and contact a second contact section, wherein the contact with the second contact section converts the kinetic energy in the torsion spring to a rotational impact on the shaft.

9. The method of claim 8, wherein the rotary impact driver comprises a handle attached to the body such that the body is rotated by rotating the handle.

10. The method of claim 8, wherein the rotary impact driver comprises an adaptation for attaching a power tool to the body such that the body is rotated by operation of the power tool.

11. method of claim 8, wherein the power tool comprises an electric drill.

12. A system for applying rotational impact to a threaded anchor, comprising:
   a torsion spring defined by a diameter and width and having a first end and a second end;
   a body comprising
      a proximal end configured for rigid attachment to a tool;
      a spring cavity disposed on a longitudinal axis for retaining at least a portion of the torsion spring;
      an opening configured for fixed connection to the first end of the torsion spring; and
      a shaft cavity disposed on the longitudinal axis for retaining at least a portion of a shaft;
   a shaft assembly comprising
      a shaft comprising a proximal end adapted for rotatable connection to the body and a distal end adapted for connection to a driver tip; and
      an impact disk rigidly connected to the shaft comprising
         one or more contact sections defined by an arc length and profile for slidable contact with the second end of the torsion spring and one or more non-contact sections of selected arc length separating the one or more contact sections, wherein rotation of the body about the shaft when the second end is in contact with a first contact section changes the torsion spring configuration to generate potential energy in the torsion spring, and wherein further rotation of the body about the shaft causes the second end to be in a non-contact section, wherein the torsion spring is configured to convert the generated potential energy into kinetic energy when the second end is in the non-contact section, causing the second end to transition across the non-contact section and contact a second contact section, wherein the contact with the second contact section converts the kinetic energy in the torsion spring to a rotary impact on the shaft; and a tool configured for attachment to the proximal end of the body.

13. system of claim 12, wherein the tool comprises a handle having a distal end configured for rigid attachment to the proximal end of the body.

14. system of claim 12, wherein the tool is operable to rotate the body at a selected rate.

* * * * *